United States Patent
Gigi et al.

(10) Patent No.: US 12,376,755 B2
(45) Date of Patent: Aug. 5, 2025

(54) INDUCTIVE SENSING SYSTEM AND METHOD

(71) Applicant: KONINKLIJKE PHILIPS N.V., Eindhoven (NL)

(72) Inventors: Ercan Ferit Gigi, Eindhoven (NL); Wouter Herman Peeters, Waalre (NL); Gerardus Johannes Nicolaas Doodeman, Veldhoven (NL); Tim Patrick Steunebrink, Eindhoven (NL); Carlijn Andrea Vernooij, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 114 days.

(21) Appl. No.: 17/916,127

(22) PCT Filed: Mar. 18, 2021

(86) PCT No.: PCT/EP2021/056915
§ 371 (c)(1),
(2) Date: Sep. 30, 2022

(87) PCT Pub. No.: WO2021/197855
PCT Pub. Date: Oct. 7, 2021

(65) Prior Publication Data
US 2023/0172477 A1    Jun. 8, 2023

(30) Foreign Application Priority Data

Apr. 1, 2020 (EP) .................................... 20167550

(51) Int. Cl.
*A61B 5/00* (2006.01)
*A61B 5/0522* (2021.01)

(52) U.S. Cl.
CPC .......... *A61B 5/0522* (2013.01); *A61B 5/7207* (2013.01)

(58) Field of Classification Search
CPC ....... A61B 5/0522; A61B 5/7207; A61B 5/05; A61B 5/7221; A61B 5/7278; A61B 5/7282
See application file for complete search history.

(56) References Cited

U.S. PATENT DOCUMENTS 9,675,282 B2    6/2017 Morren
2015/0216475 A1*  8/2015 Luna ................... A61B 5/7278
                                                       600/301

(Continued)

FOREIGN PATENT DOCUMENTS

JP    2006055504 A    3/2006
JP    2017148401 A    8/2017

(Continued)

OTHER PUBLICATIONS

International Search Report and Written Opinion for PCT/EP2021/056915; Mailing date: Apr. 30, 2021, 12 pages.

(Continued)

*Primary Examiner* — Pascal M Bui Pho
*Assistant Examiner* — Taylor Deutsch

(57) ABSTRACT

A system (8) and method is for extracting from sensed induction signals, component signals pertaining to different physiological phenomena in the body. A resonator circuit (10) is oscillated at a certain frequency to generate an alternating electromagnetic field which is applied to a body to be investigated. This field induces secondary eddy currents in the body which interact with the primary magnetic field and alter at least the frequency and amplitude of the resonator circuit oscillating current. These changes in the current characteristics, in particular the frequency and amplitude, are measured and provide first and second input signals. A system (8) or method is provided by embodiments of the invention which is arranged to receive these input signals. A multitude of different composite or fused signals are then generated by the system, each formed from a different linear combination ratio of the two input signals. These are then assessed with a signal selection procedure to identify a best candidate signal for providing a measure or indication of a particular one or more physiological phenomena. This can be based on pre-defined selection criteria, for example relating to signal characteristics of the candidate signals.

15 Claims, 6 Drawing Sheets

(56) References Cited

U.S. PATENT DOCUMENTS

| | | | |
|---|---|---|---|
| 2016/0073908 A1* | 3/2016 | Khachaturian | G01K 7/42 600/474 |
| 2017/0290543 A1 | 10/2017 | Madaus et al. | |
| 2021/0219884 A1 | 7/2021 | De Haan | |

FOREIGN PATENT DOCUMENTS

| | | |
|---|---|---|
| WO | 2012063185 A1 | 5/2012 |
| WO | 2016201130 A1 | 12/2016 |
| WO | 2018127482 A1 | 7/2018 |
| WO | 2018127488 A1 | 7/2018 |

OTHER PUBLICATIONS

Hyvarinen, A. et al., "Independent Component Analysis: Algorithms and Applications". Neural Networks 13 (2000) 411-430.

* cited by examiner

INDUCTIVE SENSING SYSTEM AND METHOD

This application is the U.S. National Phase application under 35 U.S.C. § 371 of International Application No. PCT/EP2021/056915, filed on Mar. 18, 2021, which claims the benefit of European Application 2167550.1, filed Apr. 1, 2020. These applications are hereby incorporated by reference herein.

FIELD OF THE INVENTION

This invention relates an inductive sensing system, in particular for detecting and separating signal components indicative of different physiological phenomena.

BACKGROUND OF THE INVENTION

There is commonly a need to measure mechanical movements and dynamical changes of internal bodily structures such as the heart, the lungs, or arteries. For instance, it is useful to measure the cyclically varying internal volume or dimensions of chambers of the heart, or of the lungs, or of mechanical activity of arteries, e.g. changing arterial volumes over heart cycles.

Sensors which measure mechanical activity are sometimes called kymographic sensors (kymographic biometric sensors in the clinical field). Some examples of kymographic biometric sensors are accelerometer-based biosensors, transthoracic impedance biosensors, radar-based biosensors, capacitive sensors, and photoplethysmography (PPG) sensors.

Magnetic inductive sensors also have the potential to be used as biometric sensors for sensing mechanical activity. The working principle of inductive sensing is based on Faraday's law. An oscillating primary magnetic field is generated by a generating loop antenna, and this induces, via Faraday's law, eddy currents in the tissue irradiated by the signals. The eddy currents generate a secondary magnetic field. The total magnetic field is then a superposition of the primary magnetic field and the secondary magnetic field. The changes induced in electrical characteristics of the generating antenna (the antenna current) can be measured and these used to deduce characteristics of the secondary field, and thus the stimulated tissue.

Inductive sensing provides the potential for simple contactless measurements of heart and lung mechanical activity, or the mechanical activity of a blood vessel such as the radial artery in a human arm.

A significant disadvantage of kymographic biosensors in general (including inductive sensors and other types of sensors) is that it is currently very different to distinguish sensed signals originating from different physiological sources.

For example, it is very difficult to tell apart, within a single composite returned signal, signal elements relating to mechanical activity of the heart (e.g. heart pulse) and elements relating to mechanical activity of the lungs (e.g. respiration).

In known systems, this is often performed by assuming that the heart rate is larger than the breathing rate. In this way, the different signal components can be distinguished and separated based on frequency.

However, the clinically possible ranges for the heart rate and pulse rate overlap. For example, frequencies of a particularly high breathing rate overlap with frequencies of a particularly low pulse rate, and vice versa. Therefore, a sensed (high) breathing rate can be incorrectly interpreted by state of the art systems as a low heart rate, and vice versa, leading to erroneous clinical diagnoses and interventions.

For example, in neonatal monitoring, apneas are frequently not detected by impedance based measurements, for the reason that the heart contractions characteristic of this condition are interpreted incorrectly as the patient's breathing rate.

A further, related, problem with known systems is that motion artefacts are also difficult to distinguish from true biophysical signals, such as a pulse signal or a breathing signal. Distinguishing motion artefacts from true signals is again often performed by assuming that the frequency of the artefact is different from the frequency of the biometric signal and/or that the waveform of the artefact is different (e.g. in shape characteristics) from the waveform of the biometric signal. These methods however are often unsatisfactory, because both the frequency and the waveform of the signal artefact are often similar to the frequency and waveform of the biometric signal.

For example, if a patient's step frequency during walking is close to the pulse rate, (which is commonly the case) then measurements of the pulse frequency become unreliable. Additionally, even in the case that the frequencies are different, the patient's step frequency may nonetheless be interpreted as the pulse frequency due for instance to a very similar waveform of the two. This results in an incorrect measurement of the heart rate.

An improved approach to inductive sensing is therefore required which is capable of more reliably distinguishing different physiological signals both from one another and from signal artefacts.

WO 2018/127488 A1 discloses a magnetic inductive sensing device comprising a loop antenna for inductively coupling with electromagnetic (EM) signals emitted from a medium in response to stimulation of the medium with electromagnetic excitation signals. In an embodiment two antennas are each connected with an associated oscillator for driving the antennas at different respective frequencies f1 and f2. Electromagnetic signals received back at each of the antenna in response to generated electromagnetic excitation signals will also be at the respective frequencies f1 and f2, and these are mixed with one another by a mixer and a low pass filter applied, configured to pass the differential frequency. This signal is then transferred to further signal processing elements, for instance a counter.

SUMMARY OF THE INVENTION

The invention is defined by the claims.

According to examples in accordance with an aspect of the invention, there is provided a system for use in inductive sensing, for processing electromagnetic signals returned from a body responsive to application of electromagnetic excitation signals to said body, the system arranged to receive a signal input indicative of said sensed returned signals, the returned signals corresponding to signals sensed at a loop antenna of a resonator circuit based on detecting variations in electrical characteristics of the resonator circuit as the circuit is driven to generate the excitation signals;

wherein the system is configured to implement a signal extraction procedure in which the system is configured to:

detect from the sensed return signals a first input signal, the first signal based on a frequency of the sensed returned signal, detect from the sensed return signals a second input signal, the second signal based on a sensed amplitude of the sensed returned signal, apply a signal generation procedure comprising generating a plurality of candidate signals, each candidate signal formed from a different linear combination of the first and second input signals, and apply a signal selection procedure for selecting one of the candidate signals, the selection procedure based on pre-defined criteria relating to one of more signal characteristics of the input signals, the criteria configured for isolating a signal pertaining to a particular physiological source in the body, the selected signal forming an output signal.

The system may be configured for example to signally communicate in use with an inductive sensing arrangement comprising a resonator circuit including a loop antenna, the loop antenna arranged to be driven to generate the electromagnetic excitation signals and including a signal sensing means for sensing the returned signals from the body, based on detecting variations in electrical characteristics of the resonator circuit.

The system may for example comprise a processing unit or controller for receiving the signal input indicative of the sensed returned signals and for performing the signal extraction procedure.

Embodiments of the invention provide an approach for extracting from the measured induction signals signal components from different physiological sources. This is based on collecting at least two measured input signals, a first based on frequency changes in the resonator circuit, and a second based on amplitude changes. The relative amount in which a given physiological signal will be present in each of the first and second signals will typically differ. Thus, by combining (or fusing) the two input signals in particular different ratios, it is possible to arrive at a resultant output signal in which the undesired physiological signal components are suppressed, and the desired signal component is emphasized or enhanced.

However, a simple signal combination approach such as this either relies on knowing the exact ratios in which to combine the input signals in order to filter out undesired components, or it leads to multiple possible output signals, and where it is not clear which should be used for further analysis.

Embodiments according to the present invention thus instead propose to generate a plurality of candidate signals formed from different combination ratios of the input signals and then to apply a further signal selection step for selecting a best candidate signal for a particular physiological phenomenon. This can be based on pre-determined signal characteristics. Thus a combination of signal fusion, and then signal selection based on criteria specific to the physiological phenomenon in question allows for extraction of signal components pertaining to specific physiological sources in the body.

As mentioned, the system is configured to select from among the candidate signals based on analysis of signal characteristics. In some examples, this can comprise a scoring procedure comprising scoring the candidate signals according to a determined likelihood that the signal is representative of the physiological source in question, and such that the signal with the highest score is chosen for further analysis.

The system may be arranged to receive from outside the system an input corresponding to the sensed inductive sensing signals, and the system being configured only to perform the signal extraction procedure. It may comprise a processor or controller unit for this purpose for example.

In other embodiments, the system may further include an inductive sensing arrangement for acquiring the inductive sensing signals.

In particular, according to one or more embodiments, the system may further include an inductive sensing arrangement comprising:

a resonator circuit comprising a loop antenna;

a signal generation means adapted to excite the loop antenna to generate the electromagnetic excitation signals; and a signal sensing means adapted to sense said returned signals from the body using the loop antenna, based on detecting variations in electrical characteristics of the resonator circuit.

In some examples, the system may comprise a processor, such as a microprocessor unit, configured to control the resonator circuit, signal generation means and signal sensing means to perform the signal detection, combination and selection steps outlined above.

The first and second signals may be representative of variation or change in frequency or amplitude over time. They may be representative of deviation from a starting frequency or amplitude of the resonator circuit current. They may be indicative of deviation from a natural (e.g. resonant) frequency and natural (e.g. resonant) amplitude of the resonator circuit. The amplitude signal may be a damping signal, indicative of a damping of the current over time, i.e. a change in the natural amplitude due to the returned signals. It may otherwise be referred to herein as an absorption signal as it is indicative of absorption of the energy in the applied excitation signals, resulting in change in the measurable amplitude of the current in the resonator circuit.

In accordance with one or more examples, the signal generation procedure is based on use of an independent component analysis (ICA) method.

For example, the ICA method may be used for determining the combination ratios to use for generating the signals. ICA is a well-known signal analysis method, and is based on an assumption that returned signals sensed at the resonator circuit antenna are composite signals formed of a plurality of signal components, each corresponding to a different physiological source.

ICA seeks to determine a weightvector matrix which describes how underlying physiological signal components map to the two detected input signals. With this, it is possible to reconstruct the original physiological signal components from a particular linear combination of the input signals.

An ICA procedure can be fairly intensive in terms of processing resource. Therefore as an alternative, according to a further set of embodiments, the signal generation procedure may be based on use of a pre-defined set of signal combination ratios for forming the plurality of candidate signals.

The signal combination ratios may be stored in a list for example. Alternatively, there may be a pre-defined signal protocol defining a regimen for combining the input signals in a series of different ratios. It may define a series of combination ratios in set intervals for example.

This can thus be used instead of ICA in some examples (this may increase processing speed for example), or may be used in combination with ICA to improve accuracy of signal selection in some examples.

In accordance with one or more embodiments, the criteria of the signal selection procedure may include one or more of: a frequency of the candidate signal, and a number of maxima and minima of the signal over a given time window.

In accordance with one or more embodiments, the signal extraction procedure may further comprise generating an information output indicative of the particular physiological phenomenon, based on the selected candidate signal.

In accordance with one or more embodiments, the signal extraction procedure may comprise a further step of applying a band-pass filter to the input signals, in advance of the signal generation procedure.

For example, the thresholds or parameters of the band-pass filter may be set in dependence upon the physiological phenomenon for which a signal is to be extracted. It may be based on pre-defined parameters, known to be associated with different physiological phenomena for example. This advantageously pre-suppresses signal frequency components which are known to be likely outside of the range of those associated with the physiological phenomenon in question.

In accordance with one or more embodiments, signal extraction procedure may comprise a further signal processing step, applied directly following detection of the input signals, the signal processing step configured for suppressing motion artefacts in each of the input signals.

In one set of advantageous examples, the further processing step may comprise:
receiving an input indicative of a fundamental frequency of the motion to be suppressed; and
applying a notch filter to the input signals, the notch filter having an adaptable frequency setting, wherein the notch filter is applied to the input signals at one or more multiples of the fundamental frequency.

This procedure allows for suppression of periodic motion artefacts which may be present in the input signals.

The fundamental frequency can be determined based on an input from a motion sensor (such as an accelerometer) in some examples. It may be determined by the system itself or may be simply received from outside of the system.

In advantageous examples, the selection procedure is configured, in at least one mode, for selecting a candidate signal determined to be indicative of a respiratory rate of the subject.

This may be based for example on pre-determined signal characteristics, known to be associated with respiratory signals.

The system may be configured in at least one mode to run two iterations of the signal extraction procedure, the signal selection procedure in the first and second runs being configured for selecting signals pertaining to different respective first and second physiological phenomenon.

In a preferred set of examples, in at least the second run, a bandpass filter may be applied to the sensed input signals in advance of the signal generation procedure.

In a preferred set of examples, the signal selection procedure may be configured in the first run for selecting a signal pertaining a respiration rate of the subject, and in the second run for selecting a signal pertaining to a heart rate of the subject.

Examples in accordance with a further aspect of the invention provide a method for use in inductive sensing, for processing electromagnetic signals returned from a body responsive to application of electromagnetic excitation signals to said body, the method comprising:
receiving a signal input indicative of said sensed returned signals, the returned signals corresponding to signals sensed at a loop antenna of a resonator circuit based on detecting variations in electrical characteristics of the resonator circuit as the circuit is driven to generate the excitation signals; and
implementing a signal extraction procedure comprising:
detecting from the sensed return signals a first input signal, the first signal based on a frequency of the sensed returned signal,
detecting from the sensed return signals a second input signal, the second signal based on a sensed amplitude of the sensed returned signal,
applying a signal generation procedure comprising generating a plurality of candidate signals, each candidate signal formed from a different linear combination of the first and second input signals, and
applying a signal selection procedure for selecting one of the candidate signals, the selection procedure based on pre-defined criteria relating to one of more signal characteristics of the input signals, the criteria configured for isolating a signal pertaining to a particular physiological source in the body, the selected signal forming an output signal.

The method may be only for performing the signal processing, and wherein the physical inductive signal generation and sensing is performed separately, outside the scope of the claimed method.

In a further set of embodiments however, the method may further comprise steps of:
applying electromagnetic excitation signals to a body using a resonator circuit, the resonator circuit comprising a loop antenna; and
sensing said returned signals from the body using the loop antenna, based on detecting variations in electrical characteristics of the resonator circuit.

Thus, in this further set of embodiments, the method further comprises steps for performing the steps of the physical inductive sensing itself.

Examples in accordance with a further aspect of the invention provide a computer program product comprising code means configured, when run on a processor, to cause the processor to perform the method according to any in accordance with any example or embodiment outlined above or described below, or in accordance with any claim of this application.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
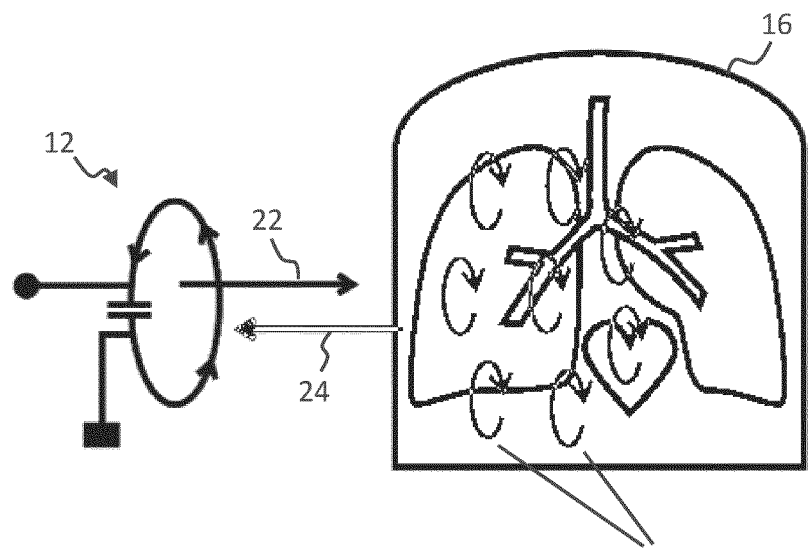
FIG. 1 schematically depicts basic principles of inductive sensing.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a system and method for extracting from sensed induction signals, component signals pertaining to different physiological phenomena in the body. A resonator circuit is oscillated at a certain frequency to generate an alternating electromagnetic field which is applied to a body to be investigated. This field induces secondary eddy currents in the body which interact with the primary magnetic field and alter at least the frequency and amplitude of the resonator circuit oscillating current. These changes in the current characteristics, in particular the frequency and amplitude, are measured and provide first and second input signals. A system or method is provided by embodiments of the invention which is arranged to receive these input signals. A multitude of different composite or fused signals are then generated by the system, each formed from a different linear combination ratio of the two input signals. These are then assessed with a signal selection procedure to identify a best candidate signal for providing a measure or indication of a particular one or more physiological phenomena. This can be based on pre-defined selection criteria, for example relating to signal characteristics of the candidate signals.

Embodiments of the invention provide a system and method for processing sensing signals acquired by an inductive sensing apparatus. In some cases, the system and method perform the steps for acquiring the inductive sensing signals. Embodiments are thus based generally on principles of magnetic induction. The basic principles of magnetic induction will first be briefly outlined.

Inductive sensing is based on the principle of inductive coupling, whereby a coil or wire has induced across it a potential difference due to exposure to a time varying magnetic field. Embodiments of the present invention use this principle to measure strength of electromagnetic signals generated within regions of a body by sensing changes in the inductance of a coil or loop antenna placed in proximity to the body, where these changes are detected based on changing resonance characteristics of the antenna or resonator circuit.

Certain embodiments of the present invention make use of a resonator comprising an antenna (which may in preferred embodiments comprise only a single turn loop) to stimulate or excite a body with electromagnetic signals (waves) and to sense signals emitted back from the body in response to those excitation signals.

The coil may be driven with an alternating current to generate the excitation signals for application to the body. These may be propagating electromagnetic signals, propagated in to the medium in some cases, or the signals can consist of a non-propagating electromagnetic field applied to the medium, i.e. by bringing the loop antenna source into proximity of the target medium. The alternating current creates a field of alternating field strength.

When the coil is brought into proximity with a body, the inductance L acquires an additional reflected inductance component, $L_r$, arising due to eddy currents induced in the stimulated body as a result of application of the excitation signals.

This is illustrated schematically in FIG. 1, which shows by way of example a loop antenna 12 being driven with an alternating current in proximity to a thorax 16 of a subject, so as to apply electromagnetic signals 22 to the thorax.

As a consequence, eddy currents 18 are induced within in the thorax.

These eddy currents in turn effectively make a contribution to the inductance of the loop antenna 12. This is because they themselves result in generation of a time-varying magnetic flux 24 of equivalent frequency to that generated by the primary antenna 12. These eddy-current fluxes combine with the primary flux of the antenna, resulting in a modified induced back-EMF in the antenna, and hence a larger measurable effective inductance.

The added component of inductance arising from the eddy currents is referred to as 'reflected inductance', $L_r$. The total inductance $L_t$ of the coil antenna 12 may be expressed as:

$$L_t = L_0 + L_r$$

where $L_0$ is the self-inductance of the coil antenna 12 in free space and $L_r$ is the reflected inductance caused by the presence of the proximate body.

In general, the reflected inductance, $L_r$, is complex, and can be expressed as $$L_r = L_r' + iL_r''$$

where $L_r'$ is related to a reactive impedance of the coil antenna and $L_r''$ is related to resistive impedance of the coil.

The addition of the reflected component of inductance $L_r$ leads to a detuning of electrical characteristics of the resonator circuit. In particular, both the natural radial frequency of the resonator circuit and the damping factor of the resonator circuit change. By measuring this detuning of the electrical characteristics, the real and imaginary parts of the reflected inductance $L_r$ can be detected.

In particular, the real part of the additional inductance component, $L_r$, manifests in the frequency of the resonator circuit or antenna. The imaginary part of the additional inductance component manifests in the amplitude of the resonator circuit. Hence, by measuring changes in the frequency and amplitude of the resonator circuit (current), and deriving a first and second input signal respectively, signals indicative of the underlying anatomical movements and phenomena are detected.

For brevity, and ease of description, embodiments of the present invention will be described below which include components or method steps for both generating and sensing inductive signals and for performing processing of the sensed signals (in particular performing a signal extraction procedure). However, it is to be understood that embodiments of the present invention may comprise only components for performing the signal processing, with the input inductive signals being received as a signal input at the system. For example, one set of embodiments may comprise just a processor or control unit configured for performing the signal extraction procedure. Thus, the description and options set out below should be understood as applying equally to embodiments in which the system comprises only means for performing the signal extraction procedure.

Figure 2:
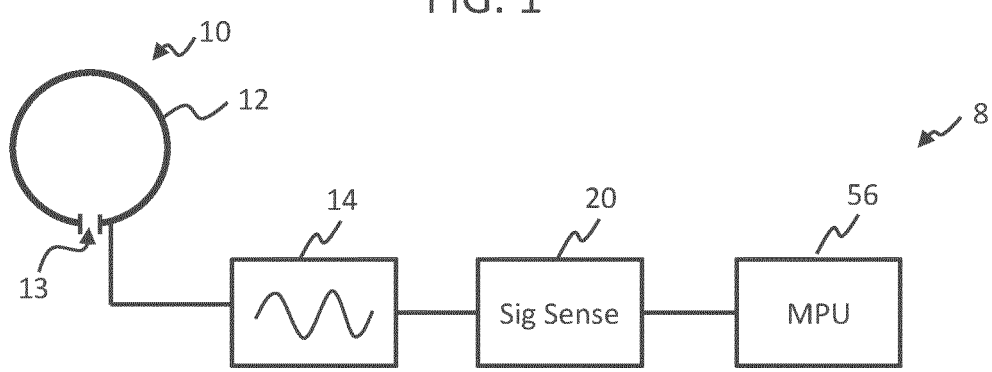
FIG. 2 schematically outlines in block diagram form components of an example inductive sensing system according to one or more embodiments.

FIG. 2 shows a block diagram of components of an example inductive sensing system 8 in accordance with one or more embodiments.

The inductive sensing system 8 is for sensing electromagnetic signals returned from a body responsive to application of electromagnetic excitation signals into said body.

The system comprises a resonator circuit 10 comprising a loop antenna 12 and an electrically coupled capacitor 13. The capacitance of the capacitor 13 at least partially defines a natural resonance frequency of the resonator circuit (in the absence of forcing or damping). When the antenna 12 is excited, it will tend to naturally resonate at the defined resonance frequency, generating electromagnetic signals at the same frequency. Selecting the capacitance of the capacitor hence allows for at least partial tuning of the frequency of the generated electromagnetic signals.

The system 8 further comprises a signal generation means 14 adapted to excite the loop antenna to generate the electromagnetic excitation signals. The signal generation means may comprise a driver means for driving the antenna, for instance at a radial frequency ω, i.e. driving the antenna with an alternating current of frequency ω. The driving means may be or comprise an oscillator for instance.

The signal generation means may drive the antenna and resonator circuit with a current of radial frequency ω where excitation signals of radial frequency ω are required.

By exciting the resonator, a resonating current is induced to flow back and forth through the loop antenna into the capacitor. By driving an alternating current through the antenna generation of oscillatory electromagnetic signals (waves) may thereby be stimulated.

The same antenna is used to generate the excitation signals as is used to sense the electromagnetic signals received from the body in response.

For the avoidance of doubt 'electromagnetic excitation signals' simply means electromagnetic signals for applying to the body for the purpose of exciting or stimulating generation of eddy currents within the body for in turn stimulating emission of electromagnetic signals back out of the body which can be sensed by the sensing system.

By 'electromagnetic signals' may generally be meant electromagnetic radiation emissions or electromagnetic near-field oscillations or electromagnetic oscillations and/or electromagnetic waves.

The system 8 further comprises a signal sensing means ("Signal Sense") 20 adapted to sense said returned signals from the body using the loop antenna 12, based on detecting variations in electrical characteristics of the resonator circuit 10. The signal sensing means may include signal processing or analysis means for detecting or monitoring electrical characteristics of the current in the resonator circuit 10.

For example, the signal sensing means 20 may be adapted to monitor at least a frequency of the resonator circuit current, and an amplitude of the resonator circuit current. These properties of the current will change in dependence upon the strength of the reflected electromagnetic signals returned from the body and detected at the antenna.

Sensing of these signal characteristics is performed at the same time (i.e. simultaneously with) excitation of the antenna for generating the excitation signals. Hence signal transmission and sensing is performed simultaneously.

Figure 3:
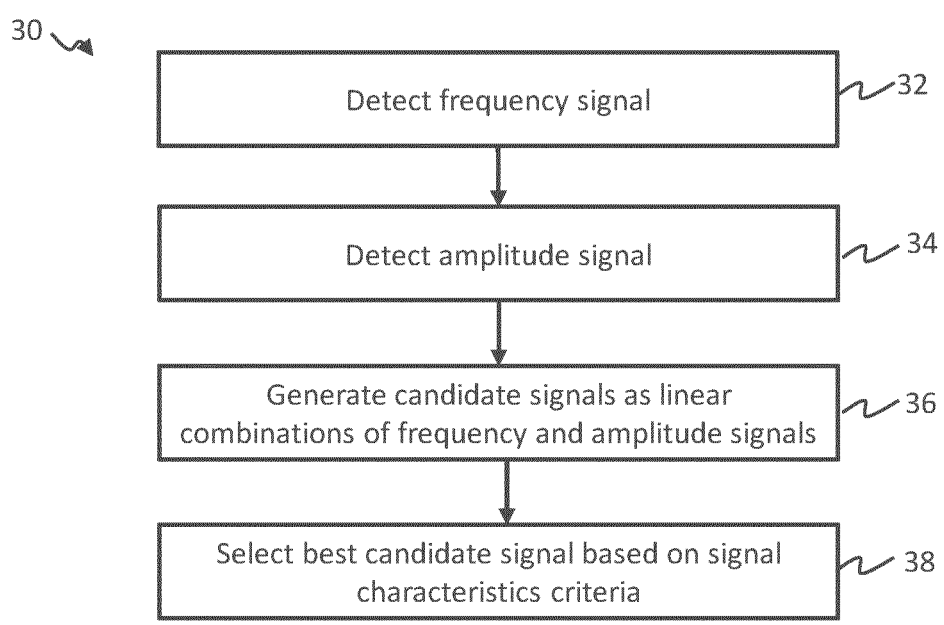
FIG. 3 outlines steps of an example signal extraction procedure as applied by a system or method in accordance with one or more embodiments.

The system is configured to implement a signal extraction procedure. For example, a processor or controller unit 56 may be provided for performing the signal extraction procedure. Steps of an example signal extraction procedure 30 in accordance with one or more embodiments are outlined in block diagram form in FIG. 3.

The system is configured to detect 32 from the sensed return signals a first input signal, the first input signal based on a frequency of the sensed returned signals.

The system is further configured to detect 34 from the sensed return signals a second input signal, the second input signal based on a sensed amplitude of the sensed returned signals at the antenna.

The system is further configured to apply 36 a signal generation procedure comprising generating a plurality of candidate signals, each candidate signal formed from a different linear combination of the first and second input signals.

The system is further configured to apply 38 a signal selection procedure for selecting one of the candidate signals. The selection procedure is based on pre-defined criteria relating to one of more signal characteristics of the input signals, the criteria configured for isolating a signal pertaining to a particular physiological source in the body. The selected signal forms an output signal. For example according to one or more applications embodiments, the selection criteria may be configured for selecting signals pertaining to respiratory rate and/or heart rate signals of the subject.

The system 8 is adapted to perform the series of steps outlined using the above components. The system may include a controller or microprocessor ("MPU") 56 adapted to perform or facilitate these steps. An example microprocessor 56 is shown in the example system of FIG. 2 for illustration. However, a dedicated controller or microprocessor is not essential. In other examples, one or more of the other components of the system, such as the signal sensing means 20 and/or signal generation means 14 may be adapted to perform the steps.

In FIG. 2, the signal sensing means 20 is shown connected to the resonator circuit 10 via the signal generation means 14. However, this is not essential: the signal sensing means and signal processing means may be independently connected to the resonator.

The signal extraction procedure may be configured in some examples for extracting a respiratory signal, e.g. respiration rate. It may in some examples be configured for extracting a heart rate. These represent just two advantageous examples.

As mentioned, according to one or more embodiments, the resonator circuit 10, the signal generation means 14 and the signal sensing means 20 may be omitted from the system 8. The system may comprise just the processor unit 56 configured to receive a signal input indicative of the sensed returned signals from the body, the returned signals corresponding to signals sensed at a loop antenna of a resonator circuit, for example based on detecting variations in electrical characteristics of the resonator circuit as the circuit is driven to generate the excitation signals.

In a preferred set of examples, the system is configured to run at least two iterations or runs of the signal extraction method, a first for extracting a signal pertaining to respiration rate of the subject and a second for extracting a signal indicative of heart rate (or vice versa).

The signal generation procedure comprises fusing or linearly combining the input signals in different ratios. This means adding together or superposing the input signals with different linear combination coefficients, e.g. a set of example candidate signals, C, generated from input signals $s_1$ and $s_2$ by this process might include:

$$C_1 = 1.0 s_1 + 1.0 s_2$$

$$C_2 = 1.5 s_1 + 1.0 s_2$$

$$C_3 = 1.0 s_1 + 1.5 s_2$$

$$\ldots$$

$$C_n = \alpha s_1 + \beta s_2$$

where $\alpha$ and $\beta$ can be positive or negative.

To explain further, the induction sensing device according to embodiments of the invention measures volumetric changes in the human body. However, the input signals sensed at the antenna typically contain components of multiple different physiological phenomena. Moreover, some phenomena have a stronger presence in the induction signals than others. For example, the respiratory signal components are stronger than the heart signal components, and so, for an antenna placed on the chest, the respiratory signal components can dominate the input signal, making it hard to detect the heart rate signals.

Likewise, for respiratory rate measurement, the presence of cardiac components is a problem. While the respiratory rate may be as high as 60 breaths/min, the cardiac rate may go as low as 30 beats/min. So the frequency range between 30 to 60 BPM is shared by both phenomena, meaning signal separation based purely on frequency is not feasible.

Signal fusion is a method where signals from various sources are combined such that unwanted components are cancelled out. The contribution of volumetric changes due to respiration and heart beats are different for frequency and absorption. Due to this difference, if the signals are linearly combined (added together or subtracted from each other with a certain factor) the resulting signal is, in most cases, more suitable for extracting one of these physiological signals (heart rate and respiration rate) than the other, and in most cases is more suitable for extracting respiratory rate than heart rate. By combining the signals with a suitable linear multiples or ratios, the signal components pertaining to the desired physiological signal can be emphasized, while those from other physiological phenomena can be suppressed.

Figure 4:
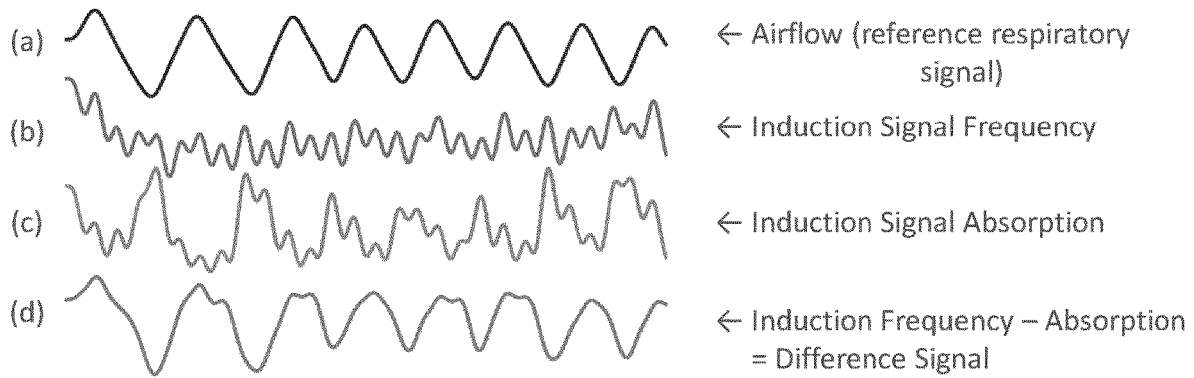
FIG. 4 illustrates example inputs signals sensed at the inductive sensor antenna, and illustrates an example candidate signal formed from a linear combination of the two.

This is schematically illustrated in FIG. 4. For reference, signal (a) shows the true respiratory signal, for example measured by an additional auxiliary sensor. Signal (b) illustrates an example $1^{st}$ input signal (indicative of a frequency of the received induction signal sensed at the antenna 12). Signal (c) illustrates an example $2^{nd}$ input signal (indicative of energy absorption by the body, e.g. an amplitude of the induction signal sensed at the antenna 12). Signal (d) illustrates an example candidate signal formed from a linear combination of input signals (a) and (b), in particular formed from a difference of the frequency signal (signal (b)) and the absorption signal (signal (c)).

The signal generation procedure 36 can be performed in different ways. In particular, one broad approach is to determine or calculate the particular combination ratio or set of ratios for the input signals for maximally emphasizing the desired physiological signal components, and then select the best signal from among this select group. An alternative broad approach is to simply generate a large number of candidate signals formed from different mixing ratios of the input signals, the ratios being random, or following a standard sequence of incrementally varying combination coefficients, and then determining the best signal from among this larger group. Examples of both of these approaches will now be outlined.

There are various methods that search for specific mixing matrices for multi-channel signals that set apart certain features contained in the signals. In the particular example, each of the input signals can be considered a multi-channel signal (i.e. containing signal components from multiple physiological sources). A mixing matrix means a set of linear combination coefficients for combining the multi-channel input signals so as to emphasize or de-emphasize certain signal components.

In accordance with one or more examples, an independent component analysis (ICA) procedure may be applied for determining the combination ratios or linear combination coefficients of the different input signals for forming the plurality of candidate signals.

ICA is a well-known signal analysis method, and is based on an assumption that returned signals sensed at the resonator circuit antenna are composite signals formed of a plurality of signal components, each corresponding to a different physiological source.

ICA seeks to determine a weightvector matrix which describes how underlying physiological signal components map to the two detected input signals. With this, it is possible to reconstruct the original physiological signal components from a particular linear combination of the input signals.

With ICA (Independent Component Analysis), the multi-channel signals (i.e. the input signals) are decomposed into independent non-Gaussian signals. According to this approach, we may consider induction frequency and absorption as the two axes of a 2D vector array.

In general terms, ICA can be understood as rotating the signal vectors so that each axis looks as non-Gaussian as possible.

According to one or more examples, the first step may be to whiten (or 'sphere') the data (i.e. the input signals). This brings the mean to zero (centering) and normalizes the variance in all directions (whitening), thereby effectively containing the vectors within a sphere around zero.

One popular method of ICA, suitable for use in the signal generation procedure according to one or more examples, is known as Fast ICA. Details of this algorithm are described in detail for example in the paper [Hyvärinen, A., & Oja, E. (2000). Independent component analysis: algorithms and applications. Neural Networks, 13, 411-430.]. It uses an efficient approximation for the entropy of the underlying source signal, and it has an effective iterative method to optimize the weightvector matrix (or an inverse of it) in order to minimize the entropy (maximize the non-Gaussianity).

In accordance with one or more examples, instead of using ICA to generate the candidate signals, the signals may be combined in random combinations, or in a standard, pre-defined sequence or set of combinations (combination ratios or coefficients).

For example, candidate signals may be generated according to a predefined signal generation protocol, the protocol defining sequentially increasing and/or decreasing linear combination coefficients for the two or more input signals. The signal generation protocol for example effectively steps through a sequence of incrementing or decrementing linear combination coefficients for each of the input signals, for instance in regular increments, thereby generating a set of candidate signals following a standard sequence of incrementing linear combination coefficients.

For example, let r represent the combination ratios, with a uniform step-size of 0.1:

$$r=[0.0, 0.1, 02, 0.3, 0.4, 0.5, 0.6, 0.7, 0.8, 0.9, 1.0]$$

Two series of signal combinations can be generated by adding and subtracting the induction frequency signal (first input signal) $I_f$ and induction absorption $I_a$ signals (second input signal):

$$s_1 = r \cdot I_f + (1-r) \cdot I_a$$

$$s_2 = r \cdot I_f - (1-r) \cdot I_a$$

It is noted that the final sign (i.e. positive or negative) of the combined (candidate) signal and also the final scale of the signal (i.e. the magnitude of the signal) is not critical. It is the relative combination ratios of the input signals included in the candidate signal which is of importance.

One possible improvement to this procedure might be to use an adaptive step size (i.e. non-uniform step size), for example based on a gradient descent search.

Where there are only a small number of input signals, for example only two input signals, as in the present example, the computational load of generating 100 different candidate signals according to a predefined signal generation protocol, such as that discussed above, is (most of the time) faster than one ICA computation. Thus, according to one or more examples, computational demand or usage may be advantageously reduced by following a random signal generation process, or following a fixed protocol or set of linear combination coefficients, instead of using an ICA procedure.

Once the candidate signals have been generated, it is necessary to decide which one (or more) to use for extracting the measurement or sample of the physiological parameter or signal in question (e.g. respiration rate or heart rate according to two examples). A signal selection procedure is thus applied.

In accordance with one or more examples, the signal selection procedure may comprise a scoring procedure or algorithm in which each candidate signal is 'scored' according to a determined likelihood of it best reflecting the physiological parameter in question, e.g. in accordance with how 'respiratory-rate-like' the signal is or how 'heart-rate-like' the signal is.

The scoring may be based for example on one or more predefined signal characteristics known to be associated with signals reflective of a particular one or more physiological phenomena. In other words, the scoring may be done by looking at features that are typical for the physiological phenomenon in question.

Signal selection procedure is advantageous to use even in the case where ICA is used to generate the initial candidate signals. This is because although ICA may be successful in separating one or more specific physiological signals from other distortions or other physiological signals (cardiac signal or motion signal for example), it does not tell which of the resulting separated signal components to use for a particular physiological phenomenon. In other words, it cannot attribute the respective sources to the different separated signal components; it cannot tell which physiological phenomenon or source of noise each separated signal components pertains to.

An extra step is thus needed to identify which of the generated candidate signals pertains to the particular physiological phenomenon for which an output signal is desired. For example, and extra step is needed to 'score' every output signal based on the extent to which it possesses signal characteristics which match those known to be associated with the physiological signal source in question.

For example, for identifying a best candidate for representing a respiratory rate of the subject, one possible approach is to analyze how 'low-frequent' the signal is. The typical frequency of the respiratory rate is lower than both the typical frequency range for cardiac pulse and for periodic motion distortions due to walking.

The scoring may be done in this example by for instance counting the maxima and minima in the signals. The signal with the lowest count gets the highest score and is selected as the output signal.

This approach is a simple and fast way of performing the signal scoring. It is simpler for example than use of band-pass filters. A band-pass filter could not by itself determine if a signal is low-frequent or not. To determine this, one would need to apply multiple band-pass filters and identify which resulting filtered signal has the highest energy, or perform a Fourier transform and analyze the spectrum. These are costly operations in terms of processing resource. Counting zero-crossings of peaks/valleys are simpler and faster alternatives.

Figure 5:
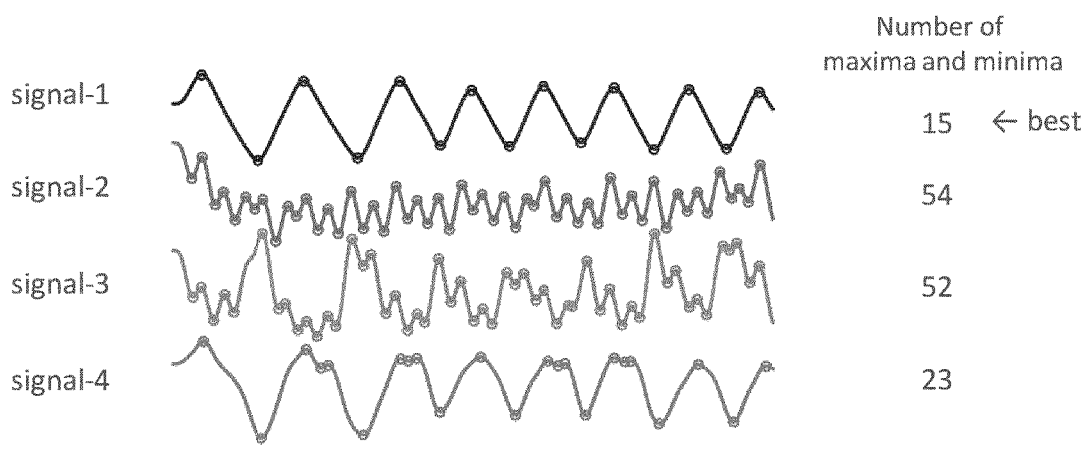
FIG. 5 illustrates a set of example candidate signals for respiratory rate, each formed from a linear combination of the at least two input signals.

This is illustrated schematically in FIG. 5 which depicts a set of four example candidate signals and sets out for each the counted number of peaks and valleys, i.e. the score. The 'best' signal is selected as the one with the lowest number of peaks and valleys, i.e. signal-1.

Where ICA is used, as discussed above, the scoring can be applied to just the two output signals of the ICA procedure, or could be applied to these two outputs in addition to the two original input signals to the ICA procedure ($I_f$ and $I_a$ from the ICA formula above). In the latter case, this means that in the event that the ICA procedure was unsuccessful in generating a better respiratory-like signal, this will not affect the final result since the original input signals can be selected as a candidate signal instead.

By way of a further example, for identifying a best candidate for indicating a heart rate signal, the scoring of the candidate fused signals for the heart rate measurement may, according to one or more examples, be performed based on two signal characteristics:

1. The frequency of the signal, for instance as indicated by the number of zero-crossings (Z),
2. Flatness (F) of the energy envelope. This is defined as the ratio between (uncorrected) standard deviation (S) and the mean absolute deviation (M) multiplied by a factor of 200 (e.g. empirically determined).

$$S = \sqrt{\frac{\Sigma_{i=0}^{N} s_i^2}{N-1}} \quad M = \Sigma_{i=0}^{N} \frac{|s_i|}{N} \quad F = 200 \frac{S}{M}$$

The different candidate signals may be scored based on their respective Z and F values, with a higher score attributed to higher Z and F values.

This approach is based on the realization that non cardiac related signal components typically exhibit a lower frequency than the heart rate signal (respiratory signals), and the signal envelope of cardiac pulses (within the time window) is in general relatively constant.

The values for the two features may be summed to form the final score:

$$score = Z + F.$$

Figure 6:
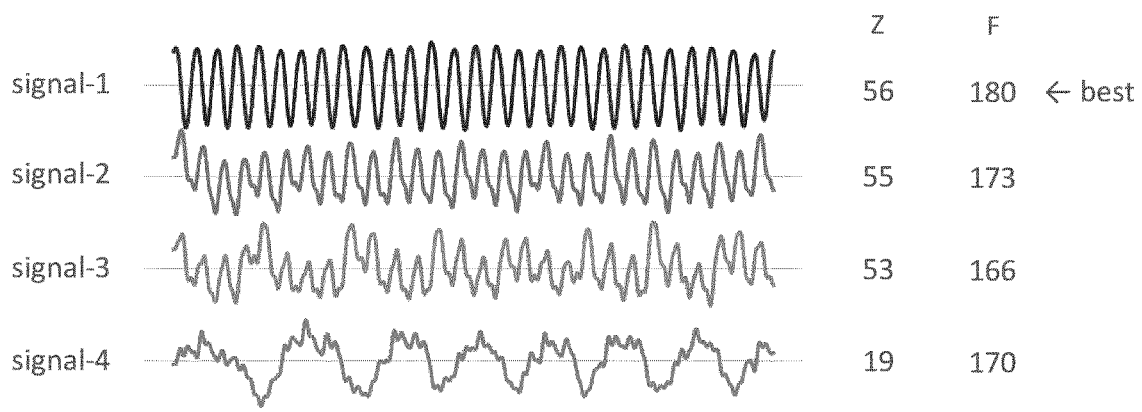
FIG. 6 illustrates a set of example candidate signals for heart rate, each formed from a linear combination of the at least two input signals.

This example approach is illustrated schematically in FIG. 6, which illustrates a set of four example candidate signals, and the respective Z and F values for each one. The 'best' candidate signal (i.e. the one with the highest Z and F values) is indicated. In this example, the selected signal is signal-1.

In accordance with one or more embodiments, the signal extraction procedure performed by the system may comprise a further signal processing step, applied directly following detection 32, 34 of the input signals, the signal processing step configured for suppressing motion artefacts in each of the input signals.

Motion suppression may be done in different ways. In accordance with one or more examples, it may comprise simple application of a filter, e.g. bandpass filter. The filter parameters may be configured for selecting frequency components in a range known to be typical for the physiological phenomenon or parameter in question, or at least for excluding one or more frequency components known to be outside of a typical range of the phenomenon in question.

One advantageous method for suppression motion artefacts in the input signals will now be briefly outlined. This approach is particularly suited for filtering or removing periodic motion artefacts, i.e. those that exhibit a periodic frequency. Such artefacts may be caused for example by walking or running of the patient (where the sensor is a portable, wearable sensor) or from other regular movements affecting the subject.

In this example, the further motion suppression processing step is based on detecting or otherwise identifying a fundamental frequency of the periodic motion to be suppressed and then applying a filter to remove frequency components around the range of this fundamental frequency.

For example, the system may be configured to receive an input indicative of a fundamental frequency of the motion to be suppressed, and to apply a filter (e.g. notch filter) to the input signals, the notch filter having an adaptable frequency setting, wherein the notch filter is applied to the input signals at one or more multiples of the fundamental frequency.

By way of example, motion artifacts related to walking and running are usually confined within certain frequency bands in the inductive sensor signals. These periodic distortions can thus be suppressed by for example an adaptive notch filter at the multiples of the fundamental frequency (f0) of the periodic motion.

The fundamental frequency $f_0$ of the periodic motion can be determined or detected by the system itself, or it may be received as an input to the system, where it has been already determined or identified externally. It might be detected by an external motion sensor element for example, and communicated to the system of the present invention.

In accordance with one or more examples, the motion frequency may be determined by the system based on an input motion signal, for instance from a motion sensor carried by the subject.

For example, the motion frequency can be measured using an input from an accelerometer, e.g. a 3D accelerometer coupled to the subject.

A 3D accelerometer measures acceleration in three directions: X, Y and Z (in the reference frame of the accelerometer). These may be termed the body axes.

The 3D accelerometer measures both the acceleration caused by gravity and the acceleration cause by movement. The gravity introduces a constant bias (g) that is spread amongst the various axes. To extract only the acceleration due to motion ($A_m$), the gravity component must be subtracted. This may be done in two steps:

First, the norm of the acceleration vector may be calculated:

$$A_n = \sqrt{A_x^2 + A_y^2 + A_z^2}$$

Second, the gravity bias may be removed by subtracting the constant gravity, and the signal rectified:

$$A_m = |A_n - g|$$

where $$g = 9.80665 \, m/s^2$$

The motion suppressing process may include an initial step of detecting whether the input signal(s) include motion artefacts which need to be suppressed. The remaining steps of the motion suppression process may then only be applied in the case that motion artefacts are detected.

By way of example, a motion threshold $T_m$ may be applied to the signal $A_m$, and wherein the motion signal $A_m$ exceeding the threshold $T_m$ (e.g. after windowing with a 10 second Hanning window) is taken as indicative that the signal has a motion artefact that needs to be suppressed.

The threshold may be pre-defined and stored locally in the system, or for example may be determined empirically. By way of example, in one example application, a volunteers study was conducted with 15 volunteers in which an indicative sensing device according to an embodiment was worn by each volunteer in combination with an accelerometer. The measurement was repeated at a frequency of once per second. As a result of this study, a threshold $T_m$ of 1 m/s$^2$ was identified. In some embodiments, a threshold $T_m$ of 1 m/s$^2$ may be used.

As mentioned, the motion frequency can be measured using the signal from a 3D accelerometer. The frequency in particular can be determined from the norm of the 3D accelerometer signal. The distortions introduced by the left and right foot may be somewhat different. In some examples, the fundamental frequency, $f_0$, measured from the acceleration may thus be divided by 2 to also suppress these.

By examining measured spectra of the acceleration frequency and the sensed induction signal frequency respectively, it has been found that the major contribution of the motion distortion is at approximately half of the motion fundamental frequency, $f_0$, e.g. in the order of approximately 50 rpm (revolutions per minute).

Numerous methods are known in the art for extracting a fundamental frequency, $f_0$, from an input signal, and the skilled person will be aware of such example methods. By way example, fundamental frequency detection is typically done based on finding a peak in the magnitude spectrum for the signal or in a time domain correlation function for the signal (such as autocorrelation).

In preferred embodiments, the fundamental frequency $f_0$ may be determined from an input acceleration signal using a particularly advantageous algorithm known as Combined Spectra Pitch Detection. Full details of this algorithm are set out in depth in the document WO 2012/063185 to which the reader is referred for further implementation details.

In brief, typical approaches to detecting the fundamental frequency, based on detecting a peak in the magnitude or time domain correlation function, can result in false detection at a multiple of the fundamental frequency. For spectral analysis, this could for instance be a higher harmonic. For time domain correlation, it may be a multiple of the repeating pulse signal.

The alternative pitch detection method (outlined in WO 2012/063185) is based on combining frequency domain and time domain signals in such a way that the resulting signal only has the $f_0$ component.

Figure 7:
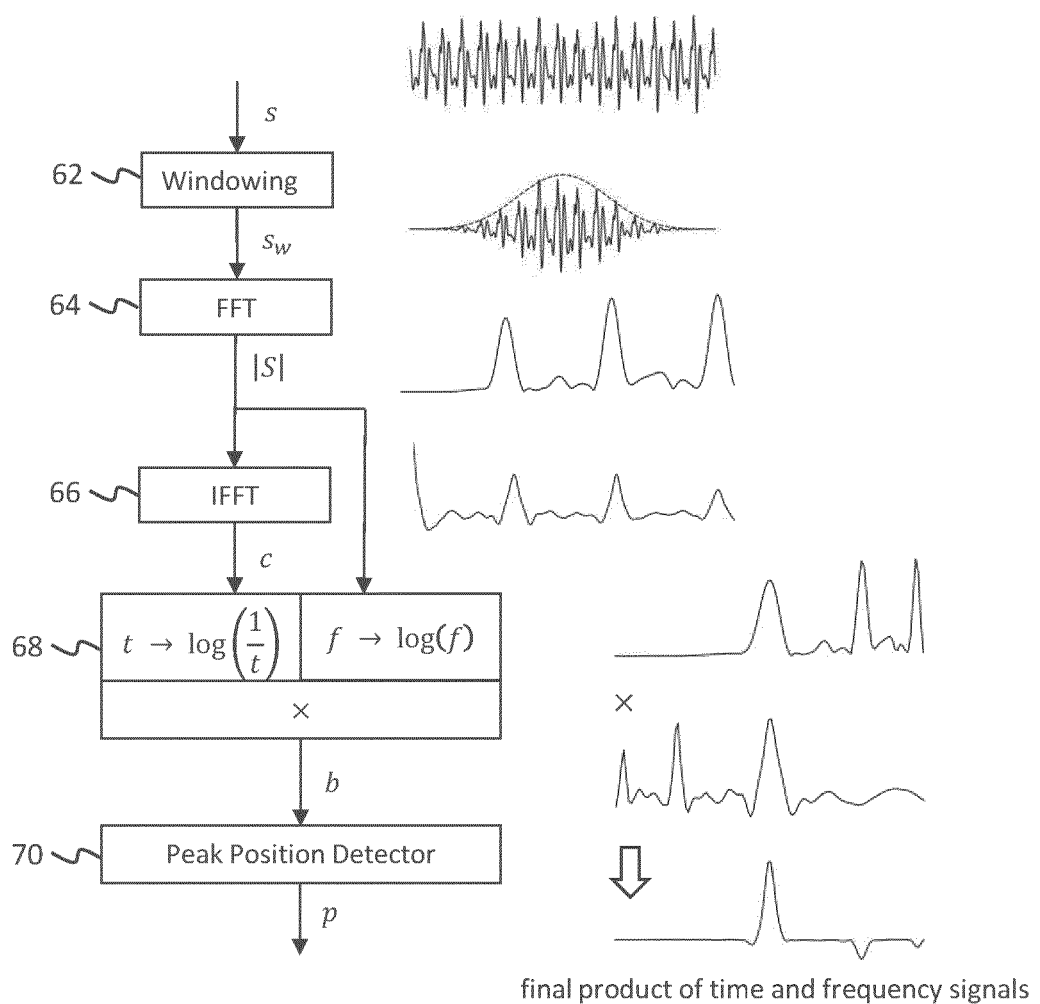
FIG. 7 outlines steps of an example procedure for determining a frequency of motion artefacts.

FIG. 7 briefly outlines in block diagram form the steps of the Combined Spectra Pitch Detection algorithm.

In a first step 62, the input signal, S, is windowed by application of a window function. Further details are found in WO 2012/063185, page 8, lines 14-30.

The resulting windowed signal, $S_W$, is then transformed from the time domain to the frequency domain in step 64, based on application of a Discrete Fourier Transformation (DFT) to provide a spectrum of the signal. For efficiency, reasons, preferably a Fast Fourier Transform (FFT) (e.g. radix 2 FFT) is used. Further details can be found in WO 2012/063185, page 8, line 31 to page 9, line 9.

A magnitude of the signal |S| is extracted. Further details can be found in WO 2012/063185, page 9, line 10 to line 25.

The window-compressed magnitude spectrum is then transformed in step 66 to the time domain using an Inverse Fourier Transformation (IFT). An Inverse Fast Fourier Transform (IFFT) may be used for example. This transformation to the time domain is used to obtain the correlation signal, c, that comprises peaks at multiples of the fundamental frequency. Further details may be found in WO 2012/063185, page 10, line 21 to page 11, line 9.

In step 68, a combined spectrum, b, is formed by multiplying the magnitude spectrum, S, and the correlation signal, c. This combined spectrum, b, has a distinct peak at the fundamental frequency. By multiplying these spectra, the higher harmonics in the frequency spectra are attenuated and the fundamental frequency remains as the predominant peak. Further details may be found in WO 2012/063185, page 11, line 18 to page 12 line 25.

Finally, in step 70, peak position detection step is performed which comprises searching for the maximum of the combined spectrum, b. This results in an output frequency value, p, in Hz, indicative of the fundamental frequency $f_0$. Further details can be found in WO 2012/063185, page 13, line 1 to page 13, line 13.

As mentioned above, once a fundamental frequency $f_0$ of the motion artefact has been detected or received by the system, the motion artefact can be suppressed in the input signals based on application of a filter having its frequency parameters set in dependence upon the fundamental frequency. For example, the filter may be a notch filter, for example an adaptable notch filter, so that the frequency parameters can be adjusted and multiple frequency components can be filtered out.

By way of example, in the case the physiological phenomenon to be measured is respiratory rate, the first and second input signals (frequency signal and amplitude or absorption signal) may each be filtered by a notch filter at $f_0$ and $f_0/2$ Hz, where $f_0$ is the fundamental of the periodic motion artifact.

Figure 8:
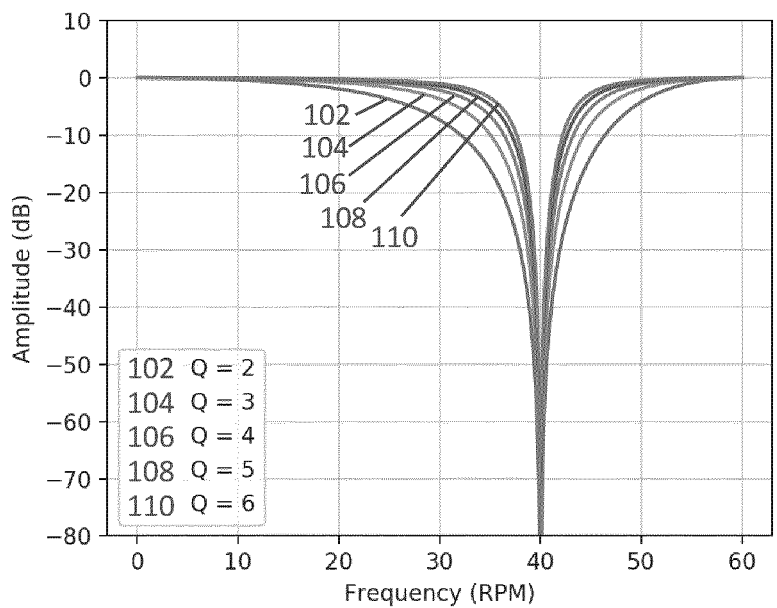
FIG. 8 illustrates example notch filter functions for use in a motion suppression procedure.

By way of illustration, FIG. 8 illustrates the function for a notch filter applied at a frequency of 40 rpm with various different quality factors, Q, from Q=2 to Q=6. The lines 102-110 shows the filter function for Q factors 2, 3, 4, 5 and 6 respectively.

By way of example, where the physiological phenomenon to be extracted is respiratory rate, Q may advantageously be set to Q=5. Where the physiological phenomenon to be extracted is heart rate, the Q may advantageously be set to Q=6 for heart rate measurements.

For heart rate calculation, preferably only $f_0/2$ Hz is suppressed. The reason for this is that the fundamental frequency, $f_0$, of relevant motion artifacts is usually much higher than the respiratory frequency, whereas for heart rate measurement, the motion $f_0$ is typically much closer to the heart rate frequency. Applying the filter at $f_0$ in the case of heart rate detection could thus lead to complete removal of the fundamental of the cardiac pulse signal itself. Thus, to avoid this, preferably the notch filter is set at only $f_0/2$ Hz.

Once the best candidate signal has been selected in the signal selection procedure (step 38 of the method of FIG. 3 above), it may be necessary to perform further steps to actually extract a measurement of the physiological phenomenon in question from the selected candidate signal.

In some examples, this may be very straightforward, and might be done for instance by simply detecting the frequency of the candidate signal (e.g. to acquire respiration rate or heart rate).

In further examples, additional processing steps may be applied to extract a more accurate or precise measure of the physiological phenomenon.

For example, where the physiological phenomenon or parameter to be acquired is a rate, e.g. respiration rate or heart rate, extraction of a measure of the physiological parameter from the candidate signal may comprise detecting a fundamental frequency $f_0$ from the selected candidate signal. This can help ensure that the derived measurement of the parameter or phenomenon is not unduly affected by noise related frequency components in the signal.

By way of one example, extraction of a respiratory rate measure or signal from a selected candidate signal will now be discussed.

Figure 9:
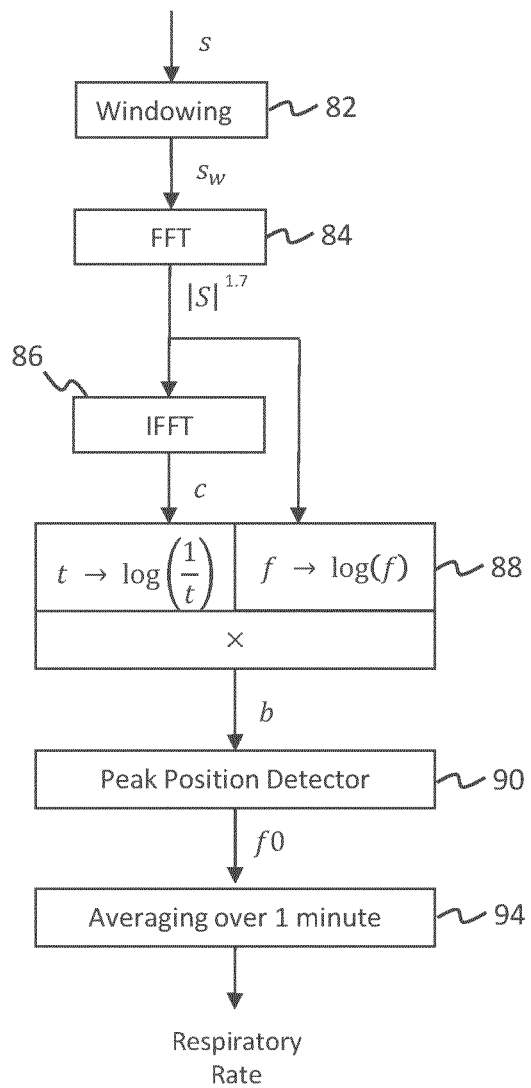
FIG. 9 outlines steps in an example procedure for extracting a respiratory rate measurement from an output signal of the signal extraction procedure.

FIG. 9 outlines steps of an example algorithm for extracting or deriving the respiration rate from a selected candidate signal, s.

The procedure is based on detecting the fundamental frequency of the selected candidate signal, s. The procedure for doing this is substantially the same as the example algorithm set out in FIG. 7 and described above. Thus similar steps will not be described in detail here and the reader is instead referred to the description provided above of the relevant steps in relation to FIG. 7.

As for the procedure of FIG. 7, the procedure begins with a windowing step 82 in which the input candidate signal, s, is time-windowed to generate windowed signal $s_W$.

The resulting windowed signal, $S_W$, is then transformed from the time domain to the frequency domain in step 84, based on application of a Discrete Fourier Transformation (DFT) to provide a spectrum of the signal. For efficiency, reasons, preferably a Fast Fourier Transform (FFT) (e.g. radix 2 FFT) is used.

A magnitude of the signal |S| is extracted. In contrast to the method of FIG. 6, the extracted magnitude is raised to the power of 1.7. This raised index will have the effect of emphasizing the spectral peaks and reducing the contribution of noise. The power value (1.7) is a value that has been identified by the inventors empirically as particularly advantageous. In the case of a respiratory signal, this will (typically) have the effect of further emphasizing the fundamental frequency component ($f_0$). For motion detection and heart-rate extraction, this emphasis is not done as the fundamental frequency in these signals may be weaker than higher harmonics.

The window-compressed magnitude spectrum is then transformed in step 86 to the time domain using an Inverse Fourier Transformation (IFT). An Inverse Fast Fourier Transform (IFFT) may be used for example. This transformation to the time domain is used to obtain the correlation signal, c, that comprises peaks at multiples of the fundamental frequency.

In step 88, a combined spectrum, b, is formed by multiplying the magnitude spectrum, S, and the correlation signal, c. This combined spectrum, b, has a distinct peak at the fundamental frequency. By multiplying these spectra, the higher harmonics in the frequency spectra are attenuated and the fundamental frequency remains as the predominant peak. Further details may be found in WO 2012/063185, page 11, line 18 to page 12 line 25.

In step 90, peak position detection step is performed which comprises searching for the maximum of the combined spectrum, b. This results in an output frequency value, $f_0$, in Hz, indicative of the fundamental frequency of the respiration rate. Further details can be found in WO 2012/063185, page 13, line 1 to page 13, line 13.

The calculated $f_0$ can be used as the final respiratory rate measurement. In some examples, the algorithm parameters may be configured to provide measurements every second, each over a window of 25 seconds (so with 24 second overlaps between windows). Each one-second measurement with 25-second window is referred to as a frame.

The method may optionally include an additional averaging step 94, in which the output over multiple frames can be averaged over a longer duration to provide a more accurate prediction. For example, the derived frequency rate values may be averaged over a window of one minute, as currently required by current World-Health-Organization (WHO) guidelines.

Figure 10:
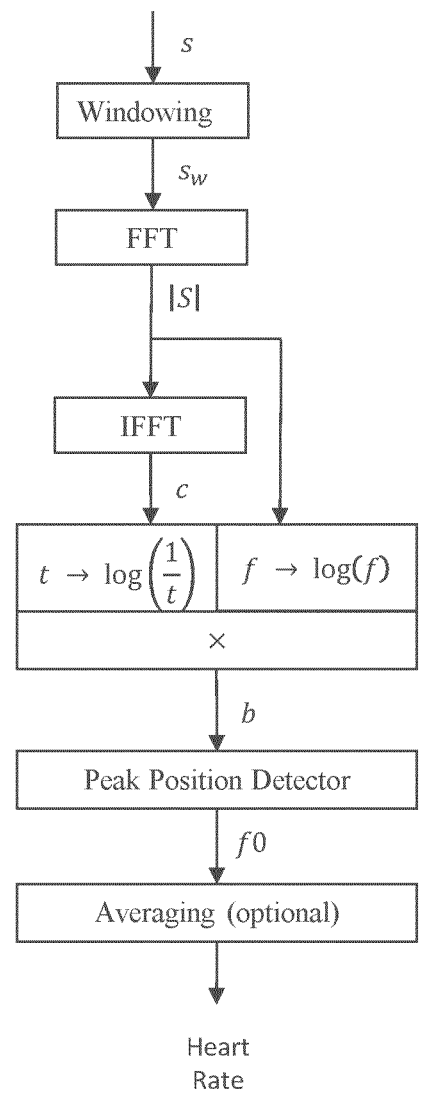
FIG. 10 outlines steps of an example method for extracting a heart rate measurement from an output signal of the signal extraction procedure.

An example procedure for extracting the heart rate from a selected candidate signal, s, is outlined in block diagram form in FIG. 10. The procedure is based on identifying the fundamental frequency, $f_0$, of the selected candidate signal, s.

The example algorithm for determining the fundamental frequency ($f_0$) for the heart rate is substantially the same as the example algorithm described above in relation to movement detection, and outlined in FIG. 7. Therefore, similar steps will not be described in detail here and the reader is instead referred to the description provided above of the relevant steps in relation to FIG. 7.

The calculated $f_0$ can be used as the final heart rate measurement. In some examples, the algorithm parameters may be configured to provide measurements every second, each over a window of 25 seconds (so with 24 second overlaps between windows). Each one second measurement with 25-second window is referred to as a frame. This example would have a corresponding (calculation) delay of 12.5 seconds.

The method may optionally include an additional averaging step, in which the output over multiple frames can be averaged over a longer duration to provide a more accurate prediction.

As mentioned above, in accordance with one or more embodiments, the signal extraction procedure may comprise a further step of applying a band-pass filter to the input signals, in advance of the signal generation procedure. The band-pass filter permits filtering out any frequency components which are known to be outside of the typical range for the physiological phenomenon in question, which renders the final extracted measurements more accurate and reliable.

The frequency band of the band-pass filter may be set in dependence upon the physiological signal to be extracted.

By way of one example, where the physiological parameter to be extracted is a respiratory rate, the band-pass filter may be set based on a typical range of breathing rates for the subject population.

Typical respiratory rates (for adults) range from 4 BPM (breaths/min) up to 60 BPM.

A band-pass filter may thus be set for removing frequency components outside this range.

By way of example, the filter may comprise for instance a cascade of two Butterworth IIR filters with a second order high-pass filter and a third order low-pass filter with an attenuation of for example −6 dB at the cutoff frequencies.

By way of example, the analysis window duration may be set at 25 seconds. The filter may be applied separately for each analysis window in forward and reverse directions (zero-phase), without introducing a filter delay.

By way of a further example, where the physiological parameter to be extracted is a heart rate, the band-pass filter may be set based on a typical range of heart or pulse rates for the subject population.

Typical heart rates (for adults) range from 30 BPM (beats/min) up to 220 BPM. A band-pass filter may thus be set to remove frequency components outside this range.

In some examples, if the lower cutoff of 30 BPM is lower than twice the respiratory rate, the latter may be used.

The filter applied may be similar to the ones used for respiratory rate measurement. For example it may comprise a cascade of two Butterworth IIR filters with a second order high-pass filter and a third order low-pass filter with an attenuation of for example −6 dB at the cutoff frequencies.

The analysis window duration is 25 seconds. The filter is applied separately for each analysis window in forward and reverse directions (zero-phase), without introducing a filter delay.

In accordance with an advantageous set of embodiments, the system may be configured in at least one mode to execute at least two runs of the signal extraction procedure, the signal selection procedure in a first and second run being configured for selecting signals pertaining to different respective first and second physiological phenomenon.

In preferred examples, in at least the second run a bandpass filter is applied to the sensed input signals in advance of the signal generation procedure.

The signal selection procedure may preferably be configured in the first run for selecting a signal pertaining a respiration rate of the subject, and in the second run for selecting a signal pertaining to a heart rate of the subject.

Figure 11:
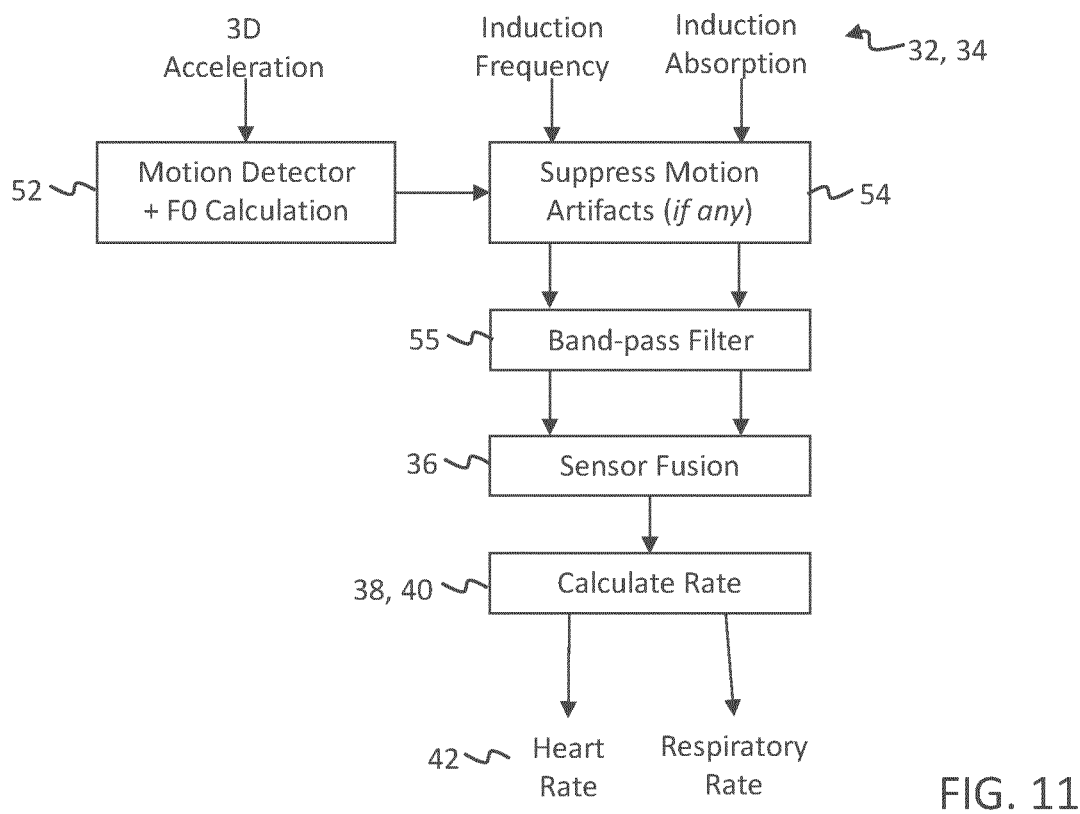
FIG. 11 illustrates steps of one example signal extraction method according to one or more embodiments.

An example signal extraction method in accordance with this approach is outlined in block diagram form in FIG. 11.

As discussed above, the method comprises applying electromagnetic excitation signals to the subject's body using a resonator circuit, the resonator circuit comprising a loop antenna.

The method further comprises sensing said returned signals from the body using the loop antenna, based on detecting variations in electrical characteristics of the resonator circuit.

From the sensed returned signals, there is detected 32 at least a first input signal, the first signal based on a frequency of the sensed returned signal, and a second input signal 34, the second signal based on a sensed amplitude of the sensed returned signal. The amplitude signal is indicative of an absorption by the body of the initially applied excitation signals.

Preferably at the same time as the input signal detection, the method may further comprise, in step 52, detecting motion of the subject (e.g. walking motion) using a motion sensor carried by the subject, for example worn by them or mounted to their person. The motion sensor may for example comprise an accelerometer, e.g. a 3D accelerometer.

If motion is detected, the system is configured to apply, in step 54, a motion suppression procedure for suppressing any motion artefacts in the detected input signals. An example motion suppression procedure was described in detail above, with reference to FIG. 7, and the reader is referred to this description for details on the motion suppression procedure of step 54.

The method then proceeds with a first run or iteration of steps for extracting a physiological signal or measure from the input signals.

In a first run, the method is configured to extract a measure of the respiratory rate for the subject.

In the first run, the method preferably comprises applying 55 a band-pass filter to each of the input signals. The frequency parameters of the band-pass filter is set for example based on a typical frequency range for the respiratory rate.

The method then comprises applying 36 a signal generation procedure comprising generating a plurality of candidate signals, each candidate signal formed from a different linear combination of the first and second input signals. In other words, the induction frequency and absorption signals (i.e. the first and second input signals) are fused into each of a set of candidate signals. This may have the effect for example that the resulting signal is free of any high frequency distortion.

Calculation of the respiratory rate is then performed.

This comprises first applying a signal selection procedure 38 for selecting one of the generated candidate signals, the selection procedure based on pre-defined criteria relating to one of more signal characteristics of the input signals, the criteria configured for isolating a signal pertaining to respiratory activity in the body. The selected signal forms an output signal. The criteria may be pre-determined or pre-defined and may for instance be based on empirical observation of typical signal characteristics which tend to be reliably associated with signals originating from respiratory action in the body.

Respiratory rate is calculated 40 using the selected candidate signal. A procedure for extracting a respiratory rate from a selected candidate signal has been described in detail earlier in this disclosure.

The method then proceeds with a second run of the signal extraction procedure, this time configured for extracting a measure or signal indicative of a heart rate of the subject.

Following the band-pass filtering 55, a signal generation procedure 36 is again applied, comprising generating a plurality of candidate signals, each formed from a different linear combination, or fusion, of the two input signals.

A heart rate is then calculated, this based on again applying a signal selection procedure 38, where the selection criteria of the procedure in this instance are configured for selecting a signal associated with heart rate. Again, these criteria may be pre-determined or pre-defined, for example based on empirical study or observation.

Once a candidate signal has been selected for calculation of the heart rate, the heart rate is then extracted 40 from the selected signal. An example procedure for extracting a heart rate measure from a selected candidate signal has been described in detail above.

The final result of the method is a set of output measures 42 indicative of a respiratory rate and heart rate respectively.

Figure 12:
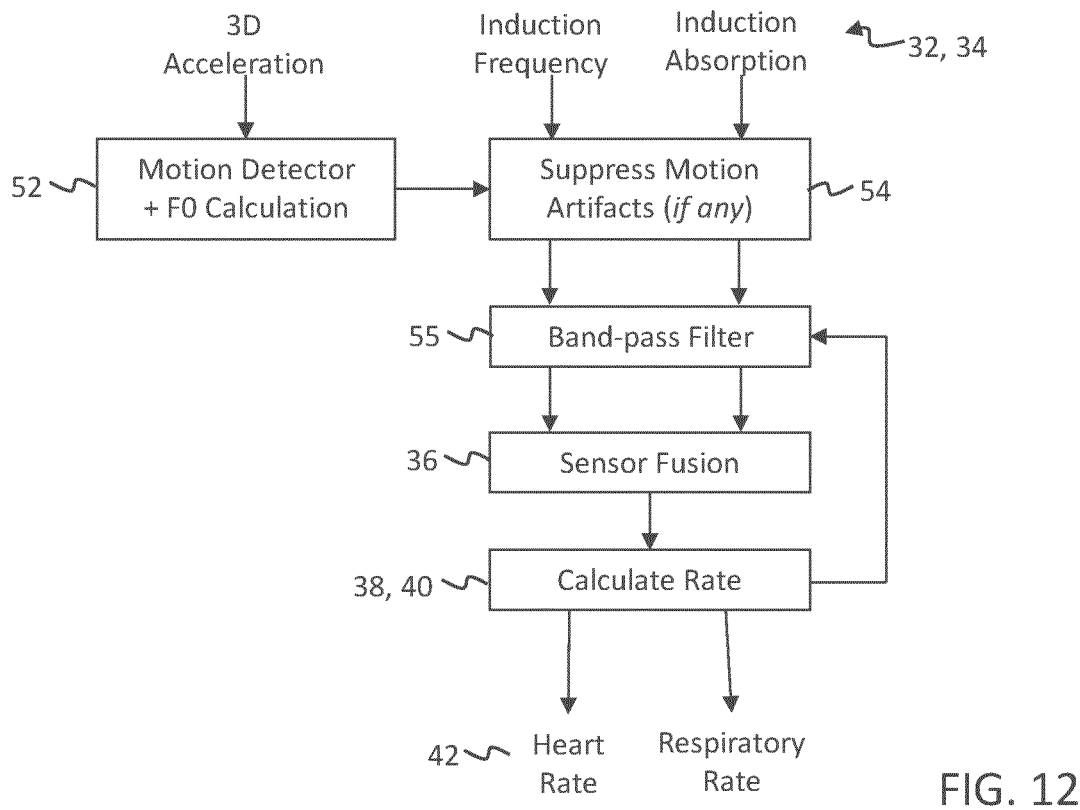
FIG. 12 illustrates steps of another example signal extraction method according to one or more embodiments.

Another example signal extraction method in accordance with this approach is outlined in block diagram form in FIG. 12, which is similar to the example signal extraction method illustrated in FIG. 11, but provides an additional feedback from the rate calculations 38, 40 to the band-pass filtering 55.

Valid heart rates (for adults) range approximately from 30 BPM up to 220 BPM. When biometric signals are used to measure the heart rate, it is advantageous to remove any frequency components from the signal that fall outside the valid range or at least limit the search space between a minimum and a maximum rate. A band-pass filter can be used to remove such unwanted frequency components. Any means that further limit this valid range will improve measurement results.

According to the embodiment illustrated in FIG. 12, it is provided that, if breathing rate is known, the breathing rate can be used to further limit the valid heart rate range. If the biometric signal that is used to derive the heart rate also contains frequency components related to respiratory rate, limiting the heart rate range is even more advantageous.

For instance, the respiratory range of an adult usually spans between 4 and 60 breaths per minute. Hence, from 30 to 60 beats per minute the fundamental frequency (f0) that is measured can belong both to heart rate as well as respiratory rate. Using the knowledge that the heart rate is at least a first factor F1 (e.g. twice) that of the respiratory rate will help suppress the first harmonic(s) (e.g. the first two harmonics) of the respiratory rate in the signal which will improve measurement accuracy of the heart rate measurement.

Likewise, limiting the upper limit of the valid heart rate frequencies using the knowledge that the heart rate is at maximum a second factor F2 (e.g. ten times) that of the respiratory rate will also improve measurement results.

Accordingly, in the embodiment illustrated in FIG. 12, the output measure 42 for the respiratory rate is fed back to the band-pass filtering 55 that uses this knowledge to filter out frequency components in the detected input signals that cannot be components of the heart rate signal for determining the heart rate signal. For instance, if the output measure 42 of the respiratory rate is R1, the value of R1 is multiplied by the first factor F1 to give a lower limit of frequencies taken into account in the detected input signals for determining the heart rate. Optionally, in addition the value of R1 is multiplied by the second factor F2 to give an upper limit of frequencies taken into account in the detected input signals for determining the heart rate.

The factors F1 and F2 can be fixed values (e.g. F1=2 and F2=10 for adults), or can set in advance or individually by a user, e.g. depending on features of the patient (e.g. age, gender, health status, etc.). The factors of 2 and/or 10 that may be applied for adults do not have to be exact. A value close to 2 and/or 10, or other individual values may be used as well.

This embodiment can preferably be applied where respiratory measurement and heart rate measurement are simultaneously done. The respiratory rate measurement generally precedes the heart rate measurement. In an exemplary implementation, the output of the respiratory rate measurement is multiplied by 2 and if this value is higher than the minimum heart rate that the system is expected to measure (e.g. 30

BPM), the 2 times the breathing rate is used. As a further improvement step, also the upper limit of the heart rate range can be limited to at most 10 times the breathing rate.

Implementation options and details for each of the above steps may be understood and interpreted in accordance with the explanations and descriptions provided previously in this disclosure with respect to the apparatus aspect of the present invention (i.e. the system aspect).

Any of the examples, options or embodiment features or details described above in respect of the apparatus aspect of this invention (in respect of the system) may be applied or combined or incorporated mutatis mutandis into the present method aspect of the invention.

Although examples above have made reference to extraction of respiratory rate and heart rate in particular, these represent only two possible examples. Embodiments of the invention may be applied to the extraction of any physiological or anatomical signal from the body, in particular those that are associated with or caused by movement of one or more bodies or features within the body. Inductive sensing is particularly suited to detecting movements of water-containing bodies.

Examples in accordance with a further aspect of the invention provide an inductive sensing method, based on sensing electromagnetic signals returned from a body responsive to application of electromagnetic excitation signals to said body.

In one set of embodiments, the method comprises receiving a signal input indicative of said sensed returned signals, the returned signals corresponding to signals sensed at a loop antenna of a resonator circuit based on detecting variations in electrical characteristics of the resonator circuit as the circuit is driven to generate the excitation signals.

The method further comprises implementing a signal extraction procedure 30.

The signal extraction procedure comprises detecting 32 from the sensed return signals a first input signal, the first signal based on a frequency of the sensed returned signal.

The signal extraction procedure further comprises detecting 34 from the sensed return signals a second input signal, the second signal based on a sensed amplitude of the sensed returned signal.

The signal extraction procedure 30 further comprises applying 36 a signal generation procedure comprising generating a plurality of candidate signals, each candidate signal formed from a different linear combination of the first and second input signals.

The signal extraction procedure further comprises applying 36 a signal selection procedure for selecting one of the candidate signals, the selection procedure based on predefined criteria relating to one of more signal characteristics of the input signals, the criteria configured for isolating a signal pertaining to a particular physiological source in the body, the selected signal forming an output signal.

According to a further set of embodiments, the method may further comprise steps for performing the physical inductive sensing, and acquiring the inductive sensing signals.

In particular, according to one or more embodiments, the method may further comprise:
applying electromagnetic excitation signals to a body using a resonator circuit, the resonator circuit comprising a loop antenna; and
sensing said returned signals from the body using the loop antenna, based on detecting variations in electrical characteristics of the resonator circuit.

Examples in accordance with a further aspect provide a computer program product comprising code means configured, when run on a processor, to cause the processor to perform the method in accordance with any example or embodiment outlined above or described below, or in accordance with any claim of this application.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A system for use in inductive sensing, for processing an electromagnetic signal returned from a body responsive to application of an electromagnetic excitation signal to said body, the system arranged to receive a signal input indicative of said sensed returned electromagnetic signal, the sensed returned electromagnetic signal corresponding to a signal sensed at a loop antenna of a resonator circuit based on detecting variations in electrical characteristics of the resonator circuit as the resonator circuit is driven to generate the electromagnetic excitation signal;

wherein the system is configured to implement a signal extraction procedure in which the system is configured to:
  detect from the sensed returned electromagnetic signal a first input signal, the first input signal based on a frequency of the sensed returned electromagnetic signal,
  detect from the sensed returned electromagnetic signal a second input signal, the second input signal based on a sensed amplitude of the sensed returned electromagnetic signal,
  apply a signal generation procedure comprising generating a plurality of candidate signals, each candidate signal of the plurality of candidate signals formed from a different linear combination of the first input signal and the second input signal, and
  apply a signal selection procedure for selecting one candidate signal of the plurality of candidate signals, the signal selection procedure based on pre-defined criteria relating to one of more signal characteristics of the first input signal and the second input signal, the pre-defined criteria configured for isolating a signal pertaining to a particular physiological source in the body, the selected one candidate signal of the plurality of candidate signals forming an output signal.

2. The system as claimed in claim 1, wherein the system further includes an inductive sensing arrangement comprising:
  the resonator circuit comprising the loop antenna;
  a signal generation means adapted to excite the loop antenna to generate the electromagnetic excitation signal; and
  a signal sensing means adapted to sense said sensed returned electromagnetic signal from the body using the loop antenna, based on detecting the variations in the electrical characteristics of the resonator circuit.

3. The system as claimed in claim 1, wherein the signal generation procedure is based on use of an independent component analysis method.

4. The system as claimed in claim 1, wherein the signal generation procedure is based on use of a pre-defined set of signal combination ratios for forming the plurality of candidate signals.

5. The system as claimed in claim 1, wherein the pre-defined criteria of the signal selection procedure include one or more of:
  a frequency of each of the plurality of candidate signals and
  a number of maxima and minima of the each of the plurality of candidate signals over a given time window.

6. The system as claimed in claim 1, wherein the signal extraction procedure further comprises generating an information output indicative of the particular physiological source, based on the selected one candidate signal of the plurality of candidate signals.

7. The system as claimed in claim 1, wherein the signal extraction procedure comprises a further step of applying a band-pass filter to the first input signal and the second input signal, in advance of the signal generation procedure.

8. The system as claimed in claim 1, wherein the signal extraction procedure comprises a further signal processing step, applied directly following the detection of the first input signal and the second input signal, the further signal processing step configured for suppressing motion artefacts in each of the first input signal and the second input signal.

9. The system as claimed in claim 8, wherein said further signal processing step comprises:
  receiving an input indicative of a fundamental frequency of the motion artefacts to be suppressed; and
  applying a notch filter to the first input signal and the second input signal, the notch filter having an adaptable frequency setting, wherein the notch filter is applied to the first input signal and the second input signal at one or more multiples of the fundamental frequency.

10. The system as claimed in claim 1, wherein the signal selection procedure is configured, in at least one mode, for selecting the one candidate signal of the plurality of candidate signals determined to be indicative of a respiratory rate of the subject.

11. The system as claimed in claim 1, wherein the system is configured in at least one mode to execute at least two runs of the signal extraction procedure, the signal selection procedure in a first run and a second run of the at least two runs being configured for selecting signals of the plurality of candidate signals pertaining to different respective first and second physiological phenomenon.

12. The system as claimed in claim 11, wherein in at least the second run a bandpass filter is applied to the first input signal and the second input signal in advance of the signal generation procedure.

13. The system as claimed in claim 11, wherein the signal selection procedure is configured in the first run for selecting a signal of the plurality of candidate signals pertaining a respiration rate of the subject, and in the second run for selecting a signal of the plurality of candidate signals pertaining to a heart rate of the subject.

14. A method for use in inductive sensing, for processing an electromagnetic signal returned from a body responsive to application of an electromagnetic excitation signal to said body, the method comprising:
  receiving a signal input indicative of said sensed returned electromagnetic signal, the sensed returned electromagnetic signal corresponding to a signal sensed at a loop antenna of a resonator circuit based on detecting variations in electrical characteristics of the resonator circuit as the resonator circuit is driven to generate the electromagnetic excitation signal; and
  implementing a signal extraction procedure comprising:
    detecting from the sensed returned electromagnetic signal a first input signal, the first input signal based on a frequency of the sensed returned electromagnetic signal,
    detecting from the sensed returned electromagnetic signal a second input signal, the second input signal based on a sensed amplitude of the sensed returned electromagnetic signal,
    applying a signal generation procedure comprising generating a plurality of candidate signals, each candidate signal of the plurality of candidate signals formed from a different linear combination of the first input signal and the second input signal, and
    applying a signal selection procedure for selecting one candidate signal of the plurality of candidate signals, the signal selection procedure based on pre-defined criteria relating to one of more signal characteristics of the first input signal and the second input signal, the pre-defined criteria configured for isolating a signal pertaining to a particular physiological source in the body, the selected one candidate signal of the plurality of candidate signals forming an output signal.

15. A non-transitory computer program product comprising code means configured, when run on a processor, to cause the processor to perform the method of claim 14.

\* \* \* \* \*